US009604085B2

(12) United States Patent
Henry et al.

(10) Patent No.: US 9,604,085 B2
(45) Date of Patent: Mar. 28, 2017

(54) METHOD AND FORMULATION FOR NEUTRALIZING TOXIC CHEMICALS AND MATERIALS

(71) Applicant: Emergent Protective Products Canada ULC, Montreal (CA)

(72) Inventors: Timothy G. Henry, Princeton, NJ (US); Barbara B. Price, Kane'ohe, HI (US)

(73) Assignee: Emergent Protective Products Canada ULC, Montreal, QC (CA)

( * ) Notice: Subject to any disclaimer, the term of this patent is extended or adjusted under 35 U.S.C. 154(b) by 0 days.

(21) Appl. No.: 13/920,416

(22) Filed: Jun. 18, 2013

(65) Prior Publication Data

US 2013/0281538 A1    Oct. 24, 2013

Related U.S. Application Data

(60) Continuation of application No. 13/284,465, filed on Oct. 28, 2011, now abandoned, which is a continuation of application No. 12/840,625, filed on Jul. 21, 2010, now abandoned, which is a division of application No. 12/017,749, filed on Jan. 22, 2008, now abandoned.

(51) Int. Cl.

| A62D 3/33 | (2007.01) |
| A62D 3/36 | (2007.01) |
| A61K 8/40 | (2006.01) |
| A61Q 17/00 | (2006.01) |
| A62D 3/30 | (2007.01) |
| A62D 101/02 | (2007.01) |
| A62D 101/04 | (2007.01) |
| A62D 101/24 | (2007.01) |
| A62D 101/43 | (2007.01) |

(52) U.S. Cl.
CPC ............ *A62D 3/36* (2013.01); *A61K 8/40* (2013.01); *A61Q 17/00* (2013.01); *A62D 3/30* (2013.01); *A62D 3/33* (2013.01); *A62D 2101/02* (2013.01); *A62D 2101/04* (2013.01); *A62D 2101/24* (2013.01); *A62D 2101/43* (2013.01)

(58) Field of Classification Search
None
See application file for complete search history.

(56) References Cited

U.S. PATENT DOCUMENTS

| 2,557,973 A | 6/1951 | Kamm |
| 2,934,451 A | 4/1960 | Prichard |
| 4,469,744 A | 9/1984 | Grot et al. |
| 4,513,047 A | 4/1985 | Leach et al. |
| 4,518,650 A | 5/1985 | Grot et al. |
| 4,789,736 A | 12/1988 | Canning et al. |
| 4,869,897 A | 9/1989 | Chatterjee et al. |
| 5,071,877 A | 12/1991 | Bannard et al. |
| 5,075,297 A * | 12/1991 | Bannard et al. ............ 514/183 |
| 5,077,316 A | 12/1991 | Bannard et al. |
| 5,364,617 A | 11/1994 | Bush et al. |
| 5,607,979 A | 3/1997 | McCreery |
| 5,695,775 A | 12/1997 | von Blüecher et al. |
| 5,902,816 A * | 5/1999 | Viner ............................ 514/334 |
| 6,017,750 A | 1/2000 | Harvey et al. |
| 6,019,941 A | 2/2000 | Porcello |
| 6,121,506 A | 9/2000 | Abel et al. |
| 6,132,750 A * | 10/2000 | Perrier et al. ................. 424/418 |
| 6,224,885 B1 | 5/2001 | Jenner et al. |
| 6,375,962 B2 | 4/2002 | Jenner et al. |
| 6,403,653 B1 | 6/2002 | Hobson et al. |
| 6,410,603 B1 | 6/2002 | Hobson et al. |
| 6,410,604 B1 | 6/2002 | Braue, Jr. et al. |

(Continued)

FOREIGN PATENT DOCUMENTS

| CA | 2 610 437 A1 | 11/2006 |
| DE | 100 10 373 C1 | 2/2002 |

(Continued)

OTHER PUBLICATIONS

"Agency for Toxic Substances and Disease Registry. Case Studies in Environmental Medicine". Oct. 17, 2007.*

Aleksashina, Z.A.; "Use of Cholinesterase Reactivators During the Poisoning of Laboratory Animals With Sevin;" Zdravookhranenie Belorussii, pp. 74-76; dated 1969.

Abele, E. et al.; "Synthesis of Heterocycles from Oximes;" Patal's Chemistry of Functional Groups: Hydroxylamines, Oximes and Hydroxamic Acids; Wiley; dated 2008

Han, X., et al.; "Degradation of the Pesticide Fenitrothion as Mediated by Cationic Surfactants and a-Nucleophilic Reagents;" Langmuir, vol. 22, No. 21; pp. 9009-9017; dated 2006.

(Continued)

*Primary Examiner* — Melvin C Mayes
*Assistant Examiner* — Sheng H Davis
(74) *Attorney, Agent, or Firm* — Sterne, Kessler, Goldstein & Fox P.L.L.C.

(57) ABSTRACT

The present invention is directed to a formulation and associated method for neutralizing one or more toxic chemical and/or materials including toxic industrial chemicals and toxic industrial materials, such as irritants, heavy metals, radioactive metals, acids and acid irritants, pesticides, and various agricultural chemicals, (collectively referred to as toxic chemical, materials, or simply toxins) as well as decontaminating surfaces that have come into contact with these agents. As a result, the formulation of the present invention can be used for neutralizing a broad spectrum of toxic chemicals and materials. In one embodiment, the active ingredient comprises 2, 3, butanedione monoxime (also known as diacetyl monoxime (DAM)), and alkali salts thereof such as potassium 2,3-butanedione monoxime (KBDO). The formulation also typically includes a carrier in which the active ingredient is dispersed. In one embodiment, the carrier comprises polyethylene glycol (PEG); monomethoxypolyethylene glycol (mPEG); and combinations and derivatives thereof.

14 Claims, No Drawings

(56) References Cited

U.S. PATENT DOCUMENTS

| | | |
|---|---|---|
| 6,414,039 B1 | 7/2002 | Braue, Jr. et al. |
| 6,417,236 B1 | 7/2002 | Hobson et al. |
| 6,420,434 B1 | 7/2002 | Braue, Jr. et al. |
| 6,437,005 B1 | 8/2002 | Hobson et al. |
| 6,451,293 B1 | 9/2002 | Schreier et al. |
| 6,472,437 B1 | 10/2002 | Braue, Jr. et al. |
| 6,472,438 B1 | 10/2002 | Braue, Jr. et al. |
| 6,479,723 B1 | 11/2002 | Malhotra et al. |
| 6,525,237 B1 | 2/2003 | Purdon et al. |
| 6,566,574 B1 | 5/2003 | Tadros et al. |
| 6,569,353 B1 | 5/2003 | Giletto et al. |
| 6,586,477 B1 | 7/2003 | Schattner |
| 6,653,519 B2 | 11/2003 | Koper et al. |
| 6,723,349 B1 | 4/2004 | Hill et al. |
| 6,723,890 B2 | 4/2004 | Tucker et al. |
| 6,723,891 B1 | 4/2004 | Wagner et al. |
| 7,125,497 B1 | 10/2006 | Tucker et al. |
| 7,435,866 B2 | 10/2008 | Ishiyama et al. |
| 8,247,365 B2 | 8/2012 | Hoffmann |
| 2001/0046995 A1 | 11/2001 | Jenner et al. |
| 2002/0031843 A1 | 3/2002 | Harmon |
| 2002/0037268 A1 | 3/2002 | Stack |
| 2003/0039619 A1 | 2/2003 | Bunger et al. |
| 2003/0049287 A1 | 3/2003 | Ley et al. |
| 2003/0054949 A1* | 3/2003 | Chang et al. ........... 502/159 |
| 2003/0055090 A1 | 3/2003 | Lin et al. |
| 2003/0083321 A1 | 5/2003 | Lerner et al. |
| 2003/0157037 A1 | 8/2003 | Bunger et al. |
| 2003/0176470 A1 | 9/2003 | Bunger et al. |
| 2004/0009095 A1 | 1/2004 | Giletto et al. |
| 2004/0022867 A1 | 2/2004 | Tucker et al. |
| 2004/0067159 A1 | 4/2004 | Carnes |
| 2004/0067205 A1 | 4/2004 | Braue, Jr. et al. |
| 2004/0185116 A1 | 9/2004 | Hill et al. |
| 2005/0032913 A1 | 2/2005 | McDonnell et al. |
| 2005/0059566 A1 | 3/2005 | Brown et al. |
| 2005/0129914 A1 | 6/2005 | Rim et al. |
| 2005/0159307 A1 | 7/2005 | Okun et al. |
| 2006/0211592 A1* | 9/2006 | Faure et al. ........... 510/421 |
| 2007/0065587 A1* | 3/2007 | Hatle ..................... 427/299 |
| 2007/0229834 A1 | 10/2007 | Patel et al. |
| 2007/0249509 A1 | 10/2007 | Tucker |
| 2008/0230689 A1 | 9/2008 | Stott et al. |
| 2008/0255431 A1 | 10/2008 | Erad et al. |
| 2009/0112042 A1 | 4/2009 | Chung et al. |
| 2011/0195035 A1* | 8/2011 | Vondruska et al. ........ 424/59 |
| 2011/0250275 A1 | 10/2011 | Cashman et al. |

FOREIGN PATENT DOCUMENTS

| | | |
|---|---|---|
| DE | 10010373 * | 2/2002 |
| EP | 0 555 208 B1 | 8/1993 |
| EP | 0 906 773 A1 | 4/1999 |
| EP | 906773 * | 4/1999 |
| GB | 686221 A | 1/1953 |
| JP | 51 149 164 A | 12/1976 |
| JP | 61-225159 A | 10/1986 |
| NL | 8900621 A | 5/1991 |
| WO | WO 92/07627 A1 | 5/1992 |
| WO | WO 93/25279 A1 | 12/1993 |
| WO | WO 97/44007 A2 | 11/1997 |
| WO | WO 01/27368 A1 | 4/2001 |
| WO | WO 02/02192 A1 | 1/2002 |
| WO | WO 03/053333 A2 | 7/2003 |
| WO | WO 03/094954 A1 | 11/2003 |
| WO | WO 2004/052918 A2 | 6/2004 |
| WO | 2004054963 * | 7/2004 |
| WO | WO 2004/060490 A1 | 7/2004 |
| WO | WO 2004/108172 A1 | 12/2004 |
| WO | WO 2005/016353 A1 | 2/2005 |
| WO | WO 2005/057588 A2 | 6/2005 |
| WO | WO 2006/031574 A2 | 2/2006 |

OTHER PUBLICATIONS

Martin, J., et al.; "Characterization and Crystal Structure of Nickel Complexes of Imine Oximes Containing Tautomerized Enolate Ligands;" Inorg. Chem., vol. 37; pp. 5811-5815; dated 1998.

Schneider, J. F. et al.; "Evaluation of an Electronic Nose With Sample Preconcentration for the Detection of Toxic Industrial Chemicals;" JPAC; pp. 20-33; dated 2005.

Pope, S., et al.; "Assay of cytotoxicity and mutagenicity of alkylating agents by using Neurospora spheroplasts;" Database CA [Online] Chemical Abstracts Service, Columbus, Ohio; XP002524504 and Mutation Research, vol. 125, No. 1; pp. 43-53 Coden: MRUEAP; dated 1984.

Terrier, F., et al.; "Revisiting the reactivity of oximate .alpha.-nucleophiles with electrophilic phosphorus centers. Relevance to detoxification of sarin, soman and DFP under mild conditions;" Database CA [Online] Chemical Abstracts Service, Columbus, Ohio; XP002524505; dated 2006.

Xiaoming, Z. et al.; "Chelating Reaction of Dimethylglyoxime with Ni(II), Pd(II, Pt(II) and Study of FT-IR Spectra of Chelate Complexes;" Nonferrous Metals (Extractive Metallurgy); pp. 32-35 and 47; dated Feb. 28, 2001.

Completed International Search Report and Written Opinion for PCT/US2008/088547 mailed on Feb. 19, 2010.

International Preliminary Report on Patentability for Application No. PCT/US2008/088547; dated Jul. 27, 2010.

Office Action for Australian Application No. 2008348284; dated Aug. 12, 2011.

Office Action for Canadian Application No. 2,712,324; dated Apr. 11, 2012.

Office Action for Chinese Application No. 200880128171.5 dated Sep. 21, 2011.

Office Action for Chinese Application No. 200880128171.5; dated May 17, 2012.

Office Action for Chinese Application No. 200880128171.5 dated Aug. 29, 2012.

Office Action for European Application No. 08 871 506.5; dated Apr. 9, 2013.

Office Action for Japanese Office Application No. 2010-544304; dated Feb. 6, 2013.

Office Action for Korean Application No. 10-2010-7018020; dated Jun. 25, 2012.

Office Action for Korean Application No. 10-2010-7018020; dated Feb. 21, 2013.

Office Action for Russian Application No. 2010134593/05 dated May 11, 2011.

Office Action for Russian Application No. 2010134593/05; dated Mar. 5, 2012.

Partial Search Report for PCT/US2008/088547; dated May 12, 2009.

Written Opinion for Singapore Application No. 201005209-0; dated Jun. 8, 2011.

English language machine translation of NL 8900621 A (listed as document FP3 on accompanying form PTO/SB/08a), accessed at https://translate.google.com/, accessed on Oct. 14, 2016, 21 pages.

Communication pursuant to Article 93(3) EPC for European Patent Appl. No. 08871506.5, European Patent Office, Rijswijk, Netherlands, dated Sep. 22, 2016, 4 pages.

* cited by examiner

METHOD AND FORMULATION FOR NEUTRALIZING TOXIC CHEMICALS AND MATERIALS

CROSS REFERENCE TO RELATED APPLICATION

This application is a continuation of U.S. application Ser. No. 13/284,465, filed Oct. 28, 2011, now abandoned, which is a continuation of U.S. application Ser. No. 12/840,625, filed Jul. 21, 2010, now abandoned, which is a divisional application of U.S. application Ser. No. 12/017,749, filed Jan. 22, 2008, now abandoned, the entire disclosure of which is hereby incorporated herein by reference.

FIELD OF THE INVENTION

The present invention relates generally to formulations and methods for neutralizing chemical agents, and more particularly, to formulations and methods for neutralizing a broad spectrum of chemical agents.

BACKGROUND OF THE INVENTION

The risk of exposure to various chemical and biological agents is an ever increasing concern for military personnel as well as civilians. This concern is particularly heightened in view of recent terrorist attacks. In particular, terrorist threats involving such agents are increasing in the United States as well as abroad. In response to this threat, various countermeasures have been developed that are capable of neutralizing certain chemical weapon agents. For example, so called nerve agents, such as sarin, soman, and tabun are examples of phosphorous containing compounds which can be altered chemically to remove their toxicity. Since many of these compounds share a common or similar chemical moiety, a single chemical countermeasure can be used to neutralize many of them.

In addition to chemical and biological agents, there also exists a wide variety of contaminants such as toxic industrial chemicals (TIC's) and toxic industrial materials (TIM's) that raise concerns over public safety. Such contaminants include industrial chemicals, pesticides, and herbicides and other materials that may be released in the environment during normal processing, disposal, waste handling, or accidental discharge. Generally, such contaminates comprise a broad spectrum of chemical compositions that are not readily neutralized or destroyed with a single chemical countermeasure. As a result, exposure to such contaminants requires that an appropriate countermeasure be selected in order to effectively neutralize the contaminant. Further, many countermeasures are only effective if they are applied prior to an exposure and are unable to effectively neutralize contaminants after a person has been exposed.

The problems with selecting an appropriate countermeasure are of particular concern in environments where a wide variety of toxic chemicals/materials are being used. For example, many modern factories use a wide variety of different chemicals and substances in their every day operation and processes. As a result, there exists a wide variety of different toxic chemical/materials to which personnel within the factory may be exposed. Since exposure to many of these chemicals/materials can result in severe injuries to the exposed workers, and in some cases death, there is a need to provide countermeasures that can be used to effectively treat individuals after exposure.

Unfortunately, this creates problems with respect to the feasibility of maintaining an adequate number of the appropriate countermeasures, as well as problems associated with educating personnel on selecting the appropriate countermeasure. Such problems can be heightened in emergency situations after an exposure has occurred. As a result, it may be difficult to find and apply the appropriate countermeasure in a timely fashion, which can result in prolonged exposure and an increase in the severity of the injury. Further, many chemical countermeasures, such as chemical disinfectants like hypochlorite solutions are useful but are corrosive to most metals and fabrics, and to human skin. Liquid-like foam disinfectants have also been used, and generally require water and pressurized gases for efficient application. As such, they are typically not practical under many circumstances.

In addition to factories, such problems can also be experienced in many households across the country. For example, the typical kitchen sink cabinet may include many different chemical/materials ranging from household cleaning products to pesticides. Similar to the chemicals/materials that may be found in a typical factory, exposure to household chemicals can also result in severe injury. However, most households today do not even include the most basic of countermeasures, and as a consequence, water is often the first choice in an attempt to cleanse exposed skin or surfaces. Since many chemical/materials do not react or are insoluble in water, the use of water can further exacerbate the exposure and severity of the injury by spreading the chemical/materials around and thereby increasing the area of contact with the toxic chemical/material.

In addition to chemical countermeasures, physical decontamination methods can also be used to neutralize many toxic chemical/materials. Physical decontamination usually involves dry heat for an extended period of time or steam or super-heated steam for about 20 minutes. In some cases, UV light can be used effectively, but it is generally difficult to implement in actual practice. Such physical decontamination methods cannot be used in the case of exposure to human skin, and are often impractical to use under many circumstances. Accordingly, there still exists a need for effective countermeasures that can be used to neutralize many of the toxic chemical/materials that may be encountered in factories, as well as in the home.

BRIEF SUMMARY OF THE INVENTION

In one alternative embodiment, the present invention is directed to a formulation and associated method for neutralizing toxic chemicals and materials, and a broad spectrum of toxic chemical and/or materials including, but not limited to, toxic industrial chemicals and toxic industrial materials, such as, for example, irritants, heavy metals, radioactive metals, acids and acid irritants, pesticides, and various agricultural chemicals, (collectively referred to as toxic chemical, materials, or simply toxins) as well as decontaminating surfaces that have come into contact with these agents. As a result, the formulation of the present invention can be used for neutralizing a wide variety of toxic chemicals and materials.

In particular, the present invention comprises a formulation having one or more active moieties that are capable of neutralizing one or more chemical agents including, but not limited to, acids, toxic industrial chemicals, toxic industrial materials, metal ions, and pesticides. In one embodiment, the formulation may include an active ingredient having a nitrogen oxime moiety and a carbonyl moiety that is capable of neutralizing a variety of toxins via a nucleophilic or electrophilic attack. In one embodiment, the active ingredient comprises 2, 3, butanedione monoxime (also known as diacetyl monoxime (DAM)), and alkali salts thereof such as potassium 2,3-butanedione monoxime (KBDO). The formulation may also include a carrier in which the active ingredient is dispersed. In one embodiment, the carrier may comprise polyethylene glycol (PEG); monomethoxypolyethylene glycol (mPEG); and combinations and derivatives thereof.

In one embodiment, the formulation of the present invention can be used to neutralize a wide variety of toxic industrial chemical and materials. In one such embodiment, DAM and its salts, such as KBDO, include three potentially nucleophilic atoms that are capable of nucleophilic attack on reactive moieties on the targeted chemical. For example, the structure of DAM includes three nucleophilic atoms: the carbonyl oxygen, the oxime nitrogen and, to a lesser extent, the oxime oxygen. The nucleophilic atoms are capable of attacking and neutralizing a wide variety of toxic chemicals. In addition to neutralizing toxins that are susceptible to nucleophilic attack, DAM and KBDO can be used to neutralize acid toxins as well. In some embodiments, DAM and KBDO can also be used to chelate metal ions and thereby can be used to effectively remove and neutralize the metal ions. In yet a further embodiment, the DAM and KBDO may be present in a carrier, such as PEG or mPEG, that is capable of solublizing and neutralizing various TICs and TIMs.

In yet another embodiment, the present invention can be used to neutralize many acids and acid anhydrides that may be encountered in a manufacturing or production environment, such as, for example, sulfuric acid ($H_2SO_4$), hydrochloric acid (HCl), hydrofluoric acid (HF), perchloric acid (HClO4), hydrobromic acid (HBr), hydroiodic acid (HI), nitric acid ($HNO_3$), nitrous acid ($HNO_2$), acetic acid, arsine ($AsH_3$), hydrogen selenide, hydrogen sulfide ($H_2S$), acid byproducts of nitrogen dioxide ($NO_2$), sulfur dioxide ($SO_2$), maleic anhydride, acetic anhydride, mixed anhydrides, and any salt, ester or derivative thereof, or any combination thereof, and the like.

In addition to neutralizing acids, the formulation may also be used to neutralize a wide variety of irritants that are commonly used in many industrial circumstances. For example, may toxic industrial or toxic materials include one or more reactive moieties that are susceptible of nucleophilic attack by one or more of the nucleophilic atoms of DAM. Such toxins may include, without limitation, 1,1'-bi(ethylene oxide), acrylonitriles, allyl alcohols, allyl chlorides, methyl mercaptan, phosgene, hydrazine, and the like, and any salt, ester or derivative thereof or any combination thereof.

In one embodiment, the formulation of the present invention may be capable of neutralizing toxins that are soluble in glycols such as hydrazine, phosphine, and toluene diisocyanates (mixed isomers). The present invention may also be used to neutralize some oxidizing and corrosive toxins.

In one alternative embodiment, the present invention is directed to a method for neutralizing a broad spectrum of toxic industrial chemicals and materials in which a composition having an active ingredient is applied to a toxic industrial chemical or material to thereby neutralize the toxic industrial chemical or and material. In one embodiment, the active ingredient comprises 2,3, butanedione monoxime or an alkali salt thereof.

In one alternative embodiment, the formulation of the present invention can be used to neutralize various metals and radionuclides, such as heavy metals, lead, transition metals, radioactive metals, Pu, Th, U, Zr, Nb, Ru, actinides, lanthanides, rare earth elements and combinations thereof, for example, via a chelating or ring forming reaction. In this embodiment, the DAM acts as a chelating agent to form a chelate complex in which the metal is bound to two or more atoms of the chelating agent. In one embodiment, DAM is capable of chelating with metal ions to form a five to seven member ring.

In one alternative embodiment, the present invention provides a method for neutralizing or sequestering metal atoms in which a composition having at least one nucleophilic carbonyl moiety and at least one nucleophilic oxime nitrogen moiety is reacted with a metal. Reaction of the composition and the metal chelates the metal to form a ring structure in which the at least one nucleophilic carbonyl moiety and at least one nucleophilic oxime nitrogen moiety are bonded to the metal.

In one alternative embodiment, the formulation of the present invention may also be used to neutralize a wide variety of pesticides. In one embodiment, formulations of the present invention can be used to neutralize pesticides containing organophosphates (OPs), pyrethroids (SP), carboxy moieties, and carbamates, or any combination thereof. In one embodiment a first DAM molecule reacts with a pesticide containing OP to produce a phosphorylated oxime. In a subsequent reaction, a second DAM molecule then reacts with the phosphonylated oxime to produce a non-toxic substituted phosphonic acid. In one embodiment, OPs pesticides that can be neutralized with DAM include, but are not limited to, azinphos-methyl, chlorpyrifos, diazinon, disulfoton, ethoprop, fonofos, malathion, methyl parathion, parathion, phorate, and terbufos.

In a further embodiment, the formulation of the present invention may also be used to neutralize pesticides containing carbamates, such as 2-methyl-2-(methylthio)propionaldehyde O-methylcarbamoyloxime (Aldicarb); 2,3-dihydro-2,2-dimethyl-7-benzofuranyl methylcarbamate (carbofuran, furadan, or curator); 3-hydroxycarbofuran; ethyl N-[2-(4-phenoxyphenoxy)ethyl]carbamate (fenoxycarb); 1-naphthyl methylcarbamate (carbaryl also known under the tradename Sevin); ethienocarb, examples: 3-hydroxycarbofuran, aldicarb sulfone, aldicarb sulfoxide, butylate, S-ethyl dipropylthiocarbamate (EPTC), methiocarb, methomyl, molinate, oxamyl, pebulate, propham, propoxur, thiobencarb, triallate. and 2-(1-methylpropyl)phenyl N-methylcarbamate.

In one alternative embodiment, the present invention is directed to a method of neutralizing a broad spectrum of pesticides, such as organophosphates, carbamates, organochlorine, and pyrethroids, in which a composition containing 2,3, butanedione monoxime or an alkali salt thereof is reacted with a pesticide to thereby neutralize the pesticide.

In one embodiment, the composition containing the active ingredient is applied in an amount that ranges from about 1:1 to 20:1 to the amount of pesticide to which a person or surface has been exposed. In some embodiments, the amount may range from about 2:1 to 15:1, and in particular from about 5:1 to 10:1. Following treatment of the toxin with the active ingredient, water may be used to remove any residual of the toxin and formulation from a surface or skin of a person that has been treated.

In one embodiment, the formulation can be provided as a topical skin protectant (TSP), such as a lotion or cream, that can be applied to human skin prior to, or after exposure to toxic chemicals or materials. In some embodiments, the formulation can be provided in the form of a liquid, gel, powder, emulsion, foam, spray, and the like. In one embodiment, the formulation can be used to decontaminate surfaces that have been exposed to toxic chemicals or materials, including but not limited to metal surface, stone surfaces, and plastic surfaces.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

In one embodiment of the invention, the formulation provides one or more decontaminants that can be used to neutralize a broad spectrum of toxic chemicals and materials. In the context of the present invention, the term "neutralization' includes the detoxification, decontamination, mitigation, or otherwise substantial destruction of toxins so that they reduce the acute adverse effects in humans or animals. Methods of neutralization include, but are not limited to, nucleophilic attack, electrophilic attack, chelating reactions, acid-base reactions, solubilization, sequestration, and combinations thereof.

In one embodiment, the formulation includes an active ingredient having a nitrogen oxime moiety and a carbonyl moiety that is capable of neutralizing a variety of toxins via a nucleophilic or electrophilic attack. In another embodiment the active ingredient includes a nitrogen oxime moiety and a carbonyl moiety. In yet another embodiment, the active ingredient comprises 2, 3, butanedione monoxime, also known as diacetyl monoxime (DAM), and salts thereof including, but not limited to, alkali salts such as potassium 2,3-butanedione monoxime (KBDO) and sodium 2,3-butanedione monoxime, and alkaline earth salts such as calcium 2,3-butanedione monoxime. The structure of DAM is illustrated by formula (1) below.

(1)

In one alternative embodiment, additional oximes that may be used in the practice of the invention include derivatives of DAM in which the alkyl group of DAM includes four to six carbon atoms. For example, in one embodiment, the active ingredient may include one or more of 2,3 pentandione monoxime, 3,4 pentandione monoxime, 3,4 hexanone monoxime, 2,3 hexananone monoxime and 4,5 hexanone monoxime (alternate names may include 2,3-pentanedione 3-oxime (CAS 609-29-0) 2 oximo pentane-3-one, 3, oximo pentane-4-one, 2,3-Pentanedione, 3-oxime, 2,4-Pentanedione oxime, Pentane-2,3-dione 2-oxime, 2,3,4-Pentanetrione, 3-oxime, 2,4-Pentanedione, dioxime, 2,4-Pentanedione, 2,4-dioxime, and combinations thereof. Unless otherwise stated, the reference to DAM herein includes diacetyl monoxime, 2,3-butanedione monoxime, salts thereof, as well as derivatives thereof. When the formulation is applied to a susceptible toxin, one or more of the reactive moieties reacts with the targeted toxin to thereby neutralize the toxin. In one embodiment, the toxin is at least substantially decomposed into end products that can be removed with water or by other means.

In one embodiment, the formulations of the present invention can be delivered and applied to the toxins in a variety of manners and phases to provide the necessary detoxification and decontamination. For example, the formulation can be in the form of a topical skin protectant (TSP), such as a lotion or cream, a liquid solution or suspension, a foam, and the like. In one alternative embodiment, formulations of the present invention may be in the form of a gel or coating. Gels and coatings suitable for the present invention are generally known in the art.

As discussed in greater detail below, an alternative embodiment of the present invention may generally comprise an activated solution or product that can be applied to a surface or skin of an individual in need thereof, or dispersed into the air to neutralize or other wise detoxify one or more toxic chemicals/materials.

In one embodiment, the formulation may generally include one or more active ingredients that are capable of binding, absorbing, solubilizing, or otherwise neutralizing a targeted chemical compound. The formulation may also typically include a carrier in which the active ingredient is dispersed. In one embodiment, the carrier comprises polyethylene glycol (PEG); monomethoxypolyethylene glycol (mPEG); and combinations and derivatives thereof. In one embodiment, the active ingredient may be dispersed in a base comprising a macrocycle chosen from 1,4,7,10,13,16-hexaoxacyclooctadecane and 4,7,13,16,21,24-hexaoxa-1,10-diazabicyclo[8.8.8]hexacosane together with a carrier chosen from dioxolane, tetraglyme, dimethoxyethane, a polyethylene glycol, or a polyethylene glycol mono- or di-ether. In another embodiment, the formulation may also include water or other solvent in amounts sufficient to ensure dissolution of the active ingredient in the base.

In one alternative embodiment, the base contains substantially equal amounts of the macrocycle and of the active ingredient. The amount of water or solvent present in the formulation is generally dependent on the desired end use of the formulation. For example, in creams and similar applications, the amount of water included may be small, such as less than about 5% of the base. In other embodiments, it may be desirable that the amount of water present be kept to a minimum as otherwise unwanted side reactions between the active ingredient and the water or solvent may occur. In some embodiments, the formulation will contain no water or solvent at all.

As discussed above, the formulation may include a carrier, such as polyethylene glycol, monomethoxypolyethylene glycol, or polyethylene glycol ether. These compounds have the formula $R-O-CH_2CH_2O)_nCH_2CH_2OR$ in which either R may be hydrogen or an alkyl group, including but not limited to methyl or ethyl, and "n" indicates the chain length. In one alternative embodiment, "n" can have a range of values. Generally, as "n" increases, the compound becomes more viscous. For example, in cream applications it may be desirable for the formulation to be relatively thick and viscous, and therefore it may be desirable to include a thickening agent. Generally, at value of "n" that represents a molecular weight of 1500 no thickening agent may be needed for the formulation to be in the form of a cream. In one embodiment, at least one of the R groups, and most preferably both, are other than hydrogen, and are typically methyl or ethyl.

In one embodiment, the formulation may be in the form of oil in water or water in oil emulsions. Other components of such emulsions may include emulsifying agents and oils conventionally used in barrier creams or lotion type formulations such as mineral or silicone oils.

In some embodiments, the formulation may also include one or more additional additives, such as surfactants, moisturizers, fragrances, fillers, coloring agents, emulsifiers, thickening agents, and the like provided the additives are inert to the active ingredient. In one alternative embodiment, the formulation may include a pharmaceutically acceptable inert solid as a thickener, which is also inert toward the active ingredient. Typical usable solids may include silicas, titania, fuller's earth, clays, bentonite and the like.

Neutralization of Toxic Industrial Chemicals and Materials

In one embodiment, formulations of the present invention can be used to neutralize a wide variety of toxic industrial chemical and materials, commonly referred to as TICS and TIMS, respectively. Many TICS and TIMS may include acids and skin irritants that can cause burning and irritation to the skin. In one embodiment, the formulation of the present invention may be used to neutralize and/or mitigate the harmful effects of these various toxins and thereby help ameliorate burns and skin irritations that may result from exposure thereto. In some embodiments, the formulation of the present invention may also be formulated to be applied to surfaces that have been exposed to TICS and TIMS. TICS and TIMS may include chemical materials found in manufacturing, production, and maintenance facilities and do not necessarily include chemical warfare agents such as, for example, vesicants (e.g., mustard gas) and nerve gas.

DAM and its salts, such as KBDO, include three potentially nucleophilic atoms that are capable of nucleophilic attack on reactive moieties on the targeted chemical. For example, the structure of DAM includes three nucleophilic atoms: the carbonyl oxygen, the oxime nitrogen and, to a lesser extent, the oxime oxygen. The nucleophilic atoms are capable of attacking and neutralizing a wide variety of toxic chemicals. In addition to neutralizing toxins that are susceptible to nucleophilic attack, DAM and KBDO can be used to neutralize acid toxins as well. In some embodiments, DAM and KBDO can also be used to chelate metal ions and as a result can be used to effectively remove and neutralize various metal ions. In yet a further embodiment, the DAM and KBDO may be present in a carrier, such as PEG or mPEG, that is capable of solublizing and neutralizing various TICs and TIMs.

In some embodiments, formulations in accordance with the present invention can be used to neutralize many acids and acid anhydrides that may be encountered in the work place. Such acids may include, without limitation, sulfuric acid ($H_2SO_4$), hydrochloric acid (HCl), hydrofluoric acid (HF), perchloric acid (HClO4), hydrobromic acid (HBr), hydroiodic acid (HI), nitric acid ($HNO_3$), nitrous acid ($HNO_2$), acetic acid, arsine ($AsH_3$), hydrogen selenide, hydrogen sulfide ($H_2S$), acid byproducts of nitrogen dioxide ($NO_2$), sulfur dioxide ($SO_2$), fluoroacetic acid, chloroacetic acid, malonic acid, formic acid, phosphoric acids, acid anhyrides such as maleic anhydride, acetic anhydride, and the like. In this embodiment, the active ingredient (e.g., DAM) and its salt KBDO are basic and are capable of reacting with acids to thereby neutralize them. In some cases, workers exposed to an acid have attempted to remove the acid by applying water, which only exacerbates the situation. In the present invention, the formulation can be applied to the skin in order to quickly neutralize the acid component and thereby help prevent further injury to the worker.

In addition to neutralizing acids, the formulation may also be used to neutralize a wide variety of irritants that are commonly used in many industrial circumstances. For example, many toxic industrial chemicals or toxic industrial materials include one or more reactive moieties that are susceptible of nucleophilic attack by one or more of the nucleophilic atoms of DAM. Typical reactive moieties that are susceptible to nucleophilic attack may include, carbonyls, allyls, epoxides, amides, nitriles, acid anhydrides, and the like. Such toxins may include, without limitation, 1,1'-bi(ethylene oxide), acrylonitriles, allyl alcohols, allyl chlorides, methyl mercaptan, acetic anhydride, fluoroacetic acid, and the like. In one embodiment, the formulation of the present invention may also be used to neutralize phosgene via a nucleophilic attack by one or more of the nucleophilic atoms of DAM.

In one alternative embodiment, formulations of the present invention can also be used to neutralize toxins that are soluble in alcohols, such as glycols. In this embodiment, the active ingredient is typically present in a glycol based carrier such as PEG or mPEG. In this embodiment, the carrier is capable of solublizing and thereby neutralizing the toxin. In one embodiment, the formulation of the present invention may be capable of neutralizing toxins such as hydrazine, phosphine, and toluene diisocyanates (mixed isomers).

In the case of hydrazine, it is believed that the active ingredient of the formulation (e.g., DAM) reacts with the basic hydrazine to help neutralize hydrazine's basicity while the glycol based carrier concomitantly assists the active ingredient by at least substantially solubilizing hydrazine. As a result, the formulation of the present invention can be used to help safely neutralize hydrazine so that the hydrazine can be removed by washing the exposed skin or surface with water.

In some embodiments, the formulation may also be used to neutralize corrosive toxins, including but not limited to, ammonia, anhydrous ammonia, and oxidizing toxins, such as chlorine.

Generally, the amount of the formulation that is needed to neutralize the toxic industrial chemicals or materials will depend on the amount of the toxic industrial chemicals or materials to which the person or surface has been exposed. In one embodiment, the composition containing the active ingredient may be applied in an amount that ranges from about 1:1 to 20:1 to the amount of toxic industrial chemicals or materials to which a person or surface has been exposed. In some embodiments, the amount may range from about 2:1 to 15:1, and in particular from about 5:1 to 10:1. In one embodiment, after application of the formulation to the toxic industrial chemical or material, water can be used to remove any residual from the skin or surface that has been treated.

Neutralization of Heavy Metals and Radioactive Metals

In one alternative embodiment, the formulation of the present invention can be used to neutralize various metal and radionuclides, such as heavy metals, lead, transition metals: radioactive metals Pu, Th, U, Zr, Nb, Ru, actinides, lanthanides, rare earths and combination thereof, for example, via a chelating or ring forming reaction. In this embodiment, the DAM acts as a chelating agent to form a chelate complex in which the metal is bound to two or more atoms of the chelating agent.

The structure of DAM can form a stable 5 to 7 ring structure with transition metals, actinides, lanthanides and heavy metals. For example, 2,3-butanedione monoxime may form a 5 membered ring with various metals, and derivatives of DAM, such as 2,4 hexanedione 2 oxime, may form 6 member ring structures. Generally, the resulting ring structure having between 5 and 7 sides provides a relatively stable reaction product in which the metal is effectively bound by the DAM. As shown in Formula (1) above, DAM includes a carbonyl oxygen and an oxime nitrogen moiety. These moieties can function as ligands that each form a bond or coordinate with the metal at more than one of the metals coordination sites. For example in the case of a lead atom, the =N and =O of DAM bind to a separate coordinate site of Pb to form a stable 5 membered ring.

Generally, metals having an empty or partially empty outer electron shell can coordinate with DAM to form a chelate complex. In one embodiment, DAM can coordinate with metals, such as transition metals, heavy metals, and actinide and transuranic metals to form a bi-dentate ligand. DAM has three nucleophilic atoms, the carbonyl oxygen, the oxime nitrogen and, to a lesser extent, the oxime oxygen. The potassium salt oximate (KBDO) has these same nucleophilic atoms and is generally believed to be more strongly nucleophilic than the neutral oxime. For example, in one embodiment DAM may chelate with Pb to form a square planar coordination complex. In yet another embodiment, a possible lead and DAM or KBDO complex is depicted below. The two dashed lines from the Pb to the oxime N and carbonyl O are the coordination bonds that form a five membered ring. In some embodiments, another molecule of DAM or KBDO can be accommodated by the Pb atom, using remaining sp3d2 orbitals to make a square planar complex as depicted below.

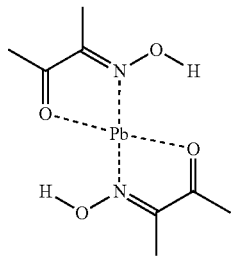

In another embodiment, DAM and KBDO may be used to complex with actinide and transuranic metals to remove them from solutions and/or surfaces. It is believed that this is especially effective in decontaminating surfaces which have been exposed to radioactive materials from a radiological weapon or radiological dispersal device (RDD), or other form of spreading radioactive materials on surfaces/areas.

Generally, the amount of the formulation that is needed to neutralize the metals will depend on the amount of the metal to which the person or surface has been exposed. In one embodiment, the composition containing the active ingredient may be applied in an amount that ranges from about 1:1 to 20:1 to the amount of metal to which a person or surface has been exposed. In some embodiments, the amount may range from about 2:1 to 15:1, and in particular from about 5:1 to 10:1. In one embodiment, after application of the composition to the metal, water can be used to remove any residual from the skin or surface that has been treated.

Neutralization of Pesticides

In one alternative embodiment, the formulation of the present invention may also be used to neutralize a wide variety of pesticides. Pesticides used in the United States are generally categorized in several major classes: organophosphates, carbamates, organochlorine, and pyrethroids. In one embodiment, formulations of the present invention can be used to neutralize pesticides containing organophosphates (OPs), pyrethroids (SP), carboxy moieties, and carbamates. Pesticides generally include chemicals and materials commonly used in insecticides, and do not necessarily include chemical warfare agents such as vesicants and nerve gas.

It is believed that in the neutralization of OP pesticides, the nitrogen oxime of DAM react with active phosphorus center of the OP in a nucleophilic attack. The nucleophilic attack results in the OP compound decomposing into reaction byproducts. In this reaction, a first molecule of DAM reacts with the OP to produce a phosphorylated oxime. In a subsequent reaction, a second DAM molecule then reacts with the phosphonylated oxime to produce a non-toxic substituted phosphonic acid. In one embodiment, OPs pesticides that can be neutralized with DAM include, but are not limited to, azinphos-methyl, chlorpyrifos, diazinon, disulfoton, ethoprop, fonofos, malathion, methyl parathion, parathion, phorate, and terbufos.

Pesticides containing carbonyls, such as carbamates, can cause cholinesterase inhibition poisoning by reversibly inactivating the enzyme acetylcholinesterase. In a further embodiment, the formulation of the present invention may also be used to neutralize pesticides containing carbamates, such as 2-methyl-2-(methylthio)propionaldehyde O-methylcarbamoyloxime (Aldicarb); 2,3-dihydro-2,2-dimethyl-7-benzofuranyl methylcarbamate (carbofuran, furadan, or curator); 3-hydroxycarbofuran; ethyl N-[2-(4-phenoxyphenoxy)ethyl]carbamate (fenoxycarb); 1-naphthyl methylcarbamate (carbaryl also known under the tradename Sevin); ethienocarb, 3-hydroxycarbofuran; aldicarb sulfone; aldicarb sulfoxide; butylate; S-ethyl dipropylthiocarbamate (EPTC); methiocarb; methomyl; molinate; oxamyl; pebulate; propham; propoxur; thiobencarb; triallate; and 2-(1-methylpropyl)phenyl N-methylcarbamate. It is believed that the carbonyl at the center of the carbonate is electrophilic and therefore susceptible to nucleophilic attack by the oxime of DAM.

In some embodiments, the carrier may also provide an effective means for neutralizing carbamates by removing or sequestering the carabate. In one embodiment, the carrier may comprise a polyglycol, such as PEG or mPEG, that is capable of solubilizing carbamates to thereby remove and neutralize the carbamate.

Generally, the amount of the formulation that is needed to neutralize the pesticides will depend on the amount of the pesticide to which the person or surface has been exposed. In one embodiment, the composition containing the active ingredient may be applied in an amount that ranges from about 1:1 to 20:1 to the amount of pesticide to which a person or surface has been exposed. In some embodiments, the amount may range from about 2:1 to 15:1, and in particular from about 5:1 to 10:1. In one embodiment, after treatment of the pesticide with the formulation, water can be used to remove residual from the skin or surface that has been treated.

As discussed above, formulations in accordance with the invention can be formulated to be delivered and applied to toxins in a variety of manners and phases. For example, the formulation can be provided as a topical skin protectant (TSP), such as a lotion or cream, that can be applied to human skin prior to, or after exposure to toxic chemicals or materials. In some embodiments, the formulation can be provided in the form of a liquid, gel, powder, emulsion, foam, spray, and the like. In one embodiment, the formulation can be used to decontaminate surfaces that have been exposed to toxic chemicals or materials.

Generally, the amount of active ingredient in the formulations is from about 1 to 90; 1 to 50; or 1 to 25 weight percent, based on the total weight of the formulation. In one embodiment, the amount of active ingredient in the formulation is between about 2 and 20 weight percent, and in particular between about 4 and 18 weight percent, and more particularly between about 5 and 15 weight percent, based on the total weight of the formulation.

Tables 1 and 2 below describe exemplary, non-limiting embodiments of the present invention in which the formulation is in the form of a cream.

TABLE 1

Cream Formulation

| Composition | Ingredient | Concentration (Wt. %) |
|---|---|---|
| Carrier | MPEG 550 | 60 to 95 |
| Active Ingredient | KBDO/DAM | 0.5 to 20 |
| Water | Water | 5 to 15 |

TABLE 2

Cream Formulation

| Ingredient | Wt. % |
|---|---|
| KBDO | 14.7 ± 0.5 |
| DAM | 0.78 to 0.95 |
| MPEG 550 | 75.98 |
| Purified Water | 8.44 |

As noted above, formulations of the present invention may be in the form of a aerosols, lotions, creams and gels. Generally, the desired viscosity of the formulations will depend on the intended use, which can be readily ascertained by one skilled in the art. For example, gels will generally have a viscosity that is greater than the viscosity of a lotion, cream, or aerosol. Table 3 below lists some exemplary viscosities for formulations that are in accordance with embodiments of the present invention.

TABLE 3

Representative Viscosities

| Form | Viscosity Range [cp] |
|---|---|
| Aerosol | <100 |
| Lotion | 100 to 5,000 |
| Cream | 5,000 to 25,000 |
| Gel | >25,000 |

In one embodiment, formulations in accordance with the present invention may have a viscosity between 140 and 180 cp at +25° C.

In one alternative embodiment, formulations in accordance with the present invention may be produced by varying blends of MPEG. For example, in one embodiment, mPEGs of varying viscosity can be blended in proportions to increase or decrease the resulting viscosity of the end product.

In one embodiment, the formulation's viscosity may be increased by physico-mechanical process of emulsification.

Tables 4 and 5 below illustrate non-limiting, exemplary formulations that are in accordance with embodiments of the present invention.

TABLE 4

Lotion base, example of formula

| Ingredient | Wt. % |
|---|---|
| Mineral oil | 25 |
| Dioctyldodecyl dodecanedioate | 2 |
| Dimethicone | 1 |
| Glyceryl stearate | 6 |
| Cetyl esters | 1 |
| Polysorbate 60 | 4 |
| Cetyl alcohol | 1 |
| Glycerin | 5 |
| Water | 55 |

TABLE 5

Cream base, example of formula

| Ingredient | Wt. % |
|---|---|
| Emulsifying wax | 2 |
| Dioctyldodecyl dodecanedioate | 5 |
| Cetearyl alcohol (and) ceteareth 20 | 2 |
| Glyceryl stearate (and) PEG 100 stearate | 1 |
| C12-15 alcohol benzoate | 2 |
| Glyceryl stearate | 2 |
| Cetyl alcohol | 2 |
| Montmorillonite | 1 |
| Water | 80 |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for neutralizing unwanted or toxic metal atoms on human skin surface or on an inanimate surface, the method comprising the steps of reacting a composition, comprising water and an active ingredient comprising one or more of 2,3-butanedione monoxime, an alkali salt thereof, and alkaline earth salt thereof, at least one nucleophilic carbonyl moiety and at least one nucleophilic oxime nitrogen moiety with a metal atom; and chelating the metal atom to form a ring structure in which the at least one nucleophilic carbonyl moiety and at least one nucleophilic oxime nitrogen moiety are bonded to the metal atom, wherein the composition comprising water is: 1) applied as a topical skin protectant to human skin prior to or after exposure to the metal atoms, or 2) applied to decontaminate a surface exposed to the metal atoms, such that the metal atoms become chelated and said skin or inanimate surface is decontaminated, wherein the active ingredient is dissolved in the water.

2. The method of claim 1, wherein the active ingredient comprises potassium 2,3-butanedione monoxime.

3. The method of claim 1, wherein the metal atom is selected from the group consisting of heavy metals, lead, transition metals, radioactive metals, Pu, Th, U, Zr, Nb, Ru, actinides, lanthanides, rare earth metals, and a combination thereof.

4. The method of claim 1, wherein the ring has 5 to 7 members.

5. The method of claim 1, wherein the composition containing the active ingredient is applied in an amount ranging from about 1:1 to 20:1 based on the amount of the metal atoms.

6. The method of claim 1, wherein the composition is applied to the skin of a person in need thereof.

7. The method of claim 1, wherein the composition is a cream, a gel, or a lotion.

8. The method of claim 1, wherein the composition comprises a carrier.

9. The method of claim 8, wherein the carrier is selected from the group consisting of polyethylene glycol, monomethoxypolyethylene glycol, polyethylene glycol ether, and combinations thereof.

10. The method of claim 9, wherein the carrier is monomethoxypolyethylene glycol.

11. The method of claim 1, further comprising the steps of: reacting the metal atom with a first and second molecule of 2,3-butanedione monoxime to form a chelated metal atom having a square planar complex.

12. The method of claim 1, further comprising removing any residual from the surface after the composition is used.

13. The method of claim 1, wherein the composition is applied to a metal, stone or plastic surface.

14. A method for neutralizing radionuclides on human skin surface or on an inanimate surface, the method comprising the steps of:

reacting a composition, comprising water and an active ingredient comprising one or more of 2,3-butanedione monoxime, an alkali salt thereof, or alkaline earth salt thereof, having at least one nucleophilic carbonyl moiety and at least one nucleophilic oxime nitrogen moiety with a radionuclide; and chelating the radionuclide to form a ring structure in which the at least one nucleophilic carbonyl moiety and at least one nucleophilic oxime nitrogen moiety are bonded to the radionuclide, wherein the composition comprising water is: 1) applied as a topical skin protectant to human skin prior to or after exposure to the radionuclides, or 2) applied to decontaminate a surface exposed to the radionuclides, such that the radionuclides become chelated and said skin or inanimate surface is decontaminated, wherein the active ingredient is dissolved in the water.

* * * * *